| (12) United States Patent<br>Jan et al. | (10) Patent No.: US 9,643,897 B2<br>(45) Date of Patent: May 9, 2017 |
|---|---|

(54) ENHANCED PROPYLENE PRODUCTION IN OTO PROCESS WITH MODIFIED ZEOLITES

(71) Applicant: UOP LLC, Des Plaines, IL (US)

(72) Inventors: Deng-Yang Jan, Elk Grove Village, IL (US); Nicholas J. Schoenfeldt, Chicago, IL (US); Jaime G. Moscoso, Mount Prospect, IL (US)

(73) Assignee: UOP LLC, Des Plaines, IL (US)

( * ) Notice: Subject to any disclaimer, the term of this patent is extended or adjusted under 35 U.S.C. 154(b) by 132 days.

(21) Appl. No.: 14/636,718

(22) Filed: Mar. 3, 2015

(65) Prior Publication Data

US 2016/0257623 A1    Sep. 8, 2016

(51) Int. Cl.
| C07C 1/20 | (2006.01) |
| B01J 29/40 | (2006.01) |
| C07C 4/02 | (2006.01) |
| C07C 6/04 | (2006.01) |
| C01B 39/36 | (2006.01) |
| B01J 29/90 | (2006.01) |
| B01J 35/00 | (2006.01) |
| B01J 35/02 | (2006.01) |
| B01J 35/10 | (2006.01) |

(52) U.S. Cl.
CPC ............... *C07C 1/20* (2013.01); *B01J 29/40* (2013.01); *B01J 29/90* (2013.01); *B01J 35/002* (2013.01); *B01J 35/023* (2013.01); *B01J 35/1057* (2013.01); *B01J 35/1061* (2013.01); *C01B 39/36* (2013.01); *C07C 4/02* (2013.01); *C07C 6/04* (2013.01); *B01J 2229/186* (2013.01); *B01J 2229/32* (2013.01); *B01J 2229/34* (2013.01); *B01J 2229/42* (2013.01); *C07C 2529/40* (2013.01); *Y02P 20/52* (2015.11); *Y02P 30/42* (2015.11)

(58) Field of Classification Search
None
See application file for complete search history.

(56) References Cited

U.S. PATENT DOCUMENTS

| 3,996,305 | A | 12/1976 | Berger |
| 4,341,914 | A | 7/1982 | Berger |
| 4,642,406 | A | 2/1987 | Schmidt |
| 4,939,110 | A | 7/1990 | Sachtler |
| 5,157,183 | A | 10/1992 | Cotterman |
| 5,417,844 | A | 5/1995 | Boitiaux |
| 5,981,817 | A | 11/1999 | Kao |
| 6,180,550 | B1 | 1/2001 | Beck |
| 6,303,839 | B1 | 10/2001 | Marker |
| 6,355,853 | B1 | 3/2002 | Sharma |
| 6,413,941 | B1 | 7/2002 | Garnett |
| 6,858,129 | B2 | 2/2005 | Mohr |
| 7,317,133 | B2 | 1/2008 | Vora |
| 7,425,660 | B2 | 9/2008 | Larson |
| 7,939,701 | B2 | 5/2011 | Whitchurch |
| 8,030,239 | B2 | 10/2011 | Oh |
| 8,134,037 | B2 | 3/2012 | Bogdan |
| 8,273,935 | B2 | 9/2012 | Rekoske |
| 8,574,542 | B2 | 11/2013 | Domokos |
| 8,692,044 | B2 | 4/2014 | Ou |
| 8,697,929 | B2 | 4/2014 | Ou |
| 8,889,937 | B2 | 11/2014 | Haizmann |
| 8,889,940 | B2 | 11/2014 | Bogdan |
| 2004/0182744 | A1 * | 9/2004 | Jan .................. C01B 39/026<br>208/111.01 |
| 2007/0060778 | A1 | 3/2007 | Bogdan |
| 2008/0146859 | A1 | 6/2008 | Rekoske |

FOREIGN PATENT DOCUMENTS

| WO | 2014035626 A1 | 3/2014 |
| WO | 2014150875 A1 | 9/2014 |

OTHER PUBLICATIONS

U.S. Appl. No. 14/636,541 filed Mar. 3, 2015, Kuzmanich.
U.S. Appl. No. 14/636,624 filed Mar. 3, 2015, Kuzmanich.
U.S. Appl. No. 14/636,672 filed Mar. 3, 2015, Moscoso.
U.S. Appl. No. 14/636,898 filed Mar. 3, 2015, Moscoso.
U.S. Appl. No. 14/636,798 filed Mar. 3, 2015, Schoenfeldt.
Raj, "Selective Formation of 1,2,4 Isomer among Trimethylbenzenes in the Methylation of Xylenes over Al- Ga-, and Fe-Silicates with MEL Structure" Journal of Catalysis, V. 138, pp. 518-524, Dec. 1992, ISSN 0021-9517, Academic Press.
Reddy, "Synthesis, Characterization, and Catalytic Properties of Metallo-Titanium Silicate Molecular Sieves with MEL Topology" Journal of Catalysis, 145, 1994, pp. 73-78.
Raj, "Catalytic Properties of [Al], [Ga], and [Fe]-silicate Analogs of ZSM-11 in C7 and C8 Aromatic Hydrocarbon Reactions: Influence of Isomorphous Substitution" Proc. Int. Zeolite Conf., 9th, 1993, 2, pp. 551-558.
Ahn, "Tailoring Mesoscopically Structured H-ZSM5 Zeolites for Toluene Methylation" Journal of Catalysis, 2014, pp. 271-280.
John, "Zeolite Containing Catalysts for the Conversion of C8-aromatics Fractions" Catalysis Today, 49, 1999 Elsevier Science B.V., pp. 211-220.
Harrison, "Some Sorptive and Catalytic Properties of Zeolite Nu-10" ZEOLITES, Jan. 1987, vol. 7, pp. 28-34.

* cited by examiner

*Primary Examiner* — Tam M Nguyen

(57) ABSTRACT

A process for oxygenate conversion using a family of crystalline aluminosilicate zeolites that is a layered pentasil zeolite with a silica or fluorine modified surface. These zeolites are represented by the empirical formula:

$$M_m{}^{n+}R_r{}^{p+}Al_{1-x}E_xSi_yO_z$$

where M is an alkali, alkaline earth, or rare earth metal such as sodium or potassium, R can be a mixture of organoammonium cations and E is a framework element such as gallium, iron, boron, or indium. These zeolites are characterized by unique x-ray diffraction patterns and compositions and have catalytic properties for carrying out oxygenate conversion processes.

19 Claims, No Drawings

ENHANCED PROPYLENE PRODUCTION IN OTO PROCESS WITH MODIFIED ZEOLITES

FIELD OF THE INVENTION

The present invention relates to the production of olefins from oxygenates. In particular, this invention relates to the use of a new material for the conversion of oxygenates to olefins with an enhanced selectivity for propylene.

BACKGROUND

The Methanol to Olefin (MTO) process is successfully commercialized by UOP. This process is covered by many UOP patents. New improvements in the catalyst compositions and process schemes are being made to improve the overall economics of the process. Flexibility in the MTO product selection to integrate the MTO plant within the existing petrochemical infrastructure is a challenge while designing new plants. The MTO process produce significant amount of $C_4$ olefins, $C_5$ olefins, aromatics and heavier species in addition to ethylene and propylene which are the desirable products. The effective utilization of these by-products can significantly improve the economics of the process.

The U.S. Pat. No. 6,303,839 issued to UOP explains an integrated MTO-Olefin cracking process. The oxygenate feed stock is catalytically converted to paraffin's, light olefins (ethylene, propylene) and heavier olefins using a silicoaluminophosphate (SAPO) molecular sieve catalyst in the vapor phase. The product is separated and the mixed butenes and heavier olefins are reacted in a second reactor to produce additional propylene. The catalyst used in the second reactor is same as that in the MTO reactor.

The U.S. Pat. No. 7,317,133 issued to UOP explains a process for enhanced olefin production. In this process, the MTO reactor product is separated in to light olefins and heavier olefins. The heavier olefins are further separated in a second stage separation to produce a $C_4$ to $C_7$ olefin stream and a heavier stream. The $C_4$ to $C_7$ olefin stream is then passed through an olefin cracking reactor (OCP) to convert a portion of the olefins to light olefins like ethylene and propylene. The catalyst in the OCP reactor is from a family of crystalline silicate of MFI or MEL like ZSM-5 or ZSM-11.

While there are many similar patents that cover integrated MTO-OCP process to maximize ethylene and propylene, none of these processes has flexibility to control the Propylene to Ethylene (P/E) product ratio. The P/E product ratio is largely determined by the MTO and OCP reactor yields. A high P/E ratio, preferably more than 3 is desirable due to the increased demand for propylene.

SUMMARY

A first embodiment of the invention is a process for the conversion of oxygenates to olefins comprising passing an oxygenate feedstream to an oxygenate conversion reactor operated at oxygenate conversion reaction conditions, wherein the reactor includes a catalyst having a layered pentasil structure and wherein the surface of the catalyst has been modified with silica or fluorine, to generate a process stream comprising olefins, wherein the catalyst is a zeolite having a microporous crystalline structure comprising a framework of $AlO_2$ and $SiO_2$ tetrahedral units, and an empirical composition in the as synthesized and anhydrous basis expressed by the empirical formula of $M_m^{n+}R_r^{p+}AlSi_yO_z$ where M is at least one exchangeable cation selected from the group consisting of alkali and alkaline earth metals, "m" is the mole ratio of M to Al and varies from 0 to 3, R is at least one organoammonium cation selected from the group consisting of quaternary ammonium cations, diquaternary ammonium cations, quaternary phosphonium cations, methonium cations, and mixtures thereof, "r" is the mole ratio of R to Al and has a value of about 0.1 to about 30, "n" is the weight average valence of M and has a value of about 1 to about 2, "p" is the weighted average valence of R and has a value of about 1 to about 2, "y" is the mole ratio of Si to Al and varies from greater than 32 to about 400 and "z" is the mole ratio of O to Al and has a value determined by the equation $z=(m·n+r·p+3+4·y)/2$. An embodiment of the invention is one, any or all of prior embodiments in this paragraph up through the first embodiment in this paragraph wherein the zeolite is further characterized in that it has the x-ray diffraction pattern having at least the d spacing and intensities set forth in the following Table A:

TABLE A

| 2Θ | d(Å) | I/Io |
|---|---|---|
| 7.92-7.99 | 11.04-11.31 | m |
| 8.79-8.88 | 9.94-11.09 | m |
| 20.28-20.56 | 4.31-4.35 | w |
| 23.10-23.18 | 3.83-3.84 | vs |
| 23.86-24.05 | 3.69-3.72 | m |
| 29.90-30.05 | 2.97-2.98 | w |
| 45.02-45.17 | 2.00-2.01 | w |

An embodiment of the invention is one, any or all of prior embodiments in this paragraph up through the first embodiment in this paragraph wherein the zeolite has a mesopore surface area between 140 m²/g and 400 m²/g. An embodiment of the invention is one, any or all of prior embodiments in this paragraph up through the first embodiment in this paragraph wherein the zeolite is made using a charge density mismatch method (U.S. Pat. No. 7,578,993), and further comprises a microporous crystalline structure comprising a framework of $AlO_2$ and $SiO_2$ tetrahedral units, further including the element E and having the empirical composition in the as synthesized and anhydrous basis expressed by the empirical formula of $M_m^{n+}R_r^{p+}Al_{1-x}E_xSi_yO_z$ where "m" is the mole ratio of M to (Al+E) and varies from 0 to 3, "r" is the mole ratio of R to (Al+E) and has a value of about 0.1 to about 30, E is an element selected from the group consisting of gallium, iron, boron, indium and mixtures thereof, "x" is the mole fraction of E and has a value from 0 to 1.0, "y" is the mole ratio of Si to (Al+E) and varies from greater than 32 to about 200 and "z" is the mole ratio of O to (Al+E) and has a value determined by the equation $z=(m·n+r·p+3+4·y)/2$. An embodiment of the invention is one, any or all of prior embodiments in this paragraph up through the first embodiment in this paragraph further comprising separating the process stream into an ethylene stream, a propylene stream, a $C_4$ stream, a $C_5$ stream, and a $C_{5+}$ heavies stream, or some combination thereof. An embodiment of the invention is one, any or all of prior embodiments in this paragraph up through the first embodiment in this paragraph further comprising passing the heavies stream, comprising $C_{4+}$ olefins, to an olefin cracking unit, or passing the $C_4$ stream and/or the $C_4^+$ stream to a metathesis unit along with some portion or all of the ethylene stream. An embodiment of the invention is one, any or all of prior embodiments in this paragraph up through the first embodiment in this paragraph wherein the oxygenates comprise alcohols, aldehydes, ethers and mixtures thereof. An embodiment of the invention is one, any or all of prior embodiments in this paragraph up through the first embodiment in this paragraph wherein the oxygenate comprises methanol. An embodiment of the invention is one, any or all of prior embodiments in this paragraph up through the first embodiment in this paragraph wherein oxygenate conversion reactor comprises a fluidized reactor bed, and wherein the oxygenate conversion reactor generate an effluent stream comprising catalyst and a process fluid, wherein the effluent stream is separated into a spent catalyst stream and the process stream comprising olefins. An embodiment of the invention is one, any or all of prior embodiments in this paragraph up through the first embodiment in this paragraph wherein the catalyst stream is passed to a regenerator to generate a regenerated catalyst stream. An embodiment of the invention is one, any or all of prior embodiments in this paragraph up through the first embodiment in this paragraph further comprising passing the regenerated catalyst stream to a stripper, to generate a stripped catalyst stream comprising catalyst with carbon oxides removed. An embodiment of the invention is one, any or all of prior embodiments in this paragraph up through the first embodiment in this paragraph further comprising passing the stripped catalyst stream to the oxygenate conversion reactor. An embodiment of the invention is one, any or all of prior embodiments in this paragraph up through the first embodiment in this paragraph wherein the oxygenate conversion reaction conditions include a temperature in the range from 300° C. to 600° C. An embodiment of the invention is one, any or all of prior embodiments in this paragraph up through the first embodiment in this paragraph wherein the oxygenate conversion reaction conditions include an oxygenate partial pressure in the range from 100 kPa to 800 kPa.

A second embodiment of the invention is a process for the conversion of oxygenates to olefins comprising passing an oxygenate feedstream to an oxygenate conversion reactor operated at oxygenate conversion reaction conditions, wherein the reactor includes a catalyst having a 2-D layered MFI structure and wherein the surface of the catalyst has been modified with silica or fluorine, to generate a process stream comprising olefins, wherein the catalyst is a zeolite of claim 1 having a microporous crystalline structure comprising a framework of $AlO_2$ and $SiO_2$ tetrahedral units, further including the element E and having the empirical composition in the as synthesized and anhydrous basis expressed by the empirical formula of $M_m^{n+}R_r^{p+}Al_{1-x}E_xSi_yO_z$; wherein m" is the mole ratio of M to (Al+E) and varies from 0 to 1, "r" is the mole ratio of R to (Al+E) and has a value of 0.1 to about 30, "n" is the weight average valence of M and has a value of 1 to 2, "p" is the weighted average valence of R and has a value of 1 to 2, "x" is the mole fraction of E and has a value from 0 to 1.0, "y" is the mole ratio of Si to (Al+E) and varies from greater than 32 to about 200 and "z" is the mole ratio of O to (Al+E) and has a value determined by the equation $$z=(m \cdot n+r \cdot p+3+4 \cdot y)/2$$

and it is characterized in that it has the x-ray diffraction pattern having at least the d spacing and intensities set forth in the following Table A:

TABLE A

| 2Θ | d(Å) | I/Io |
|---|---|---|
| 7.92-7.99 | 11.04-11.31 | m |
| 8.79-8.88 | 9.94-11.09 | m |
| 20.28-20.56 | 4.31-4.35 | w |
| 23.10-23.18 | 3.83-3.84 | vs |
| 23.86-24.05 | 3.69-3.72 | m |
| 29.90-30.05 | 2.97-2.98 | w |
| 45.02-45.17 | 2.00-2.01 | w |

An embodiment of the invention is one, any or all of prior embodiments in this paragraph up through the second embodiment in this paragraph wherein the oxygenate conversion reaction conditions include a temperature in the range from 300° C. to 600° C. An embodiment of the invention is one, any or all of prior embodiments in this paragraph up through the second embodiment in this paragraph wherein the oxygenate conversion reaction conditions include an oxygenate partial pressure in the range from 100 kPa to 800 kPa. An embodiment of the invention is one, any or all of prior embodiments in this paragraph up through the second embodiment in this paragraph further comprising separating the process stream into an ethylene stream, a propylene stream, a $C_4$ stream, a $C_5$ stream, and a $C_{5+}$ heavies stream, or some combination thereof. An embodiment of the invention is one, any or all of prior embodiments in this paragraph up through the second embodiment in this paragraph further comprising passing the heavies stream, comprising $C_{4+}$ olefins, to an olefin cracking unit, or passing the $C_4$ stream and/or the $C_4^+$ stream to a metathesis unit along with some portion or all of the ethylene stream. An embodiment of the invention is one, any or all of prior embodiments in this paragraph up through the second embodiment in this paragraph wherein the oxygenates comprises methanol.

Other objects, advantages and applications of the present invention will become apparent to those skilled in the art from the following detailed description.

DETAILED DESCRIPTION

With the increased demand for propylene, the problem to shift the selectivity towards propylene entailed adding other process schemes. The U.S. Pat. No. 7,586,018 issued to UOP explains an integrated MTO-ethylene dimerization-olefin metathesis process. In this process, a portion of the ethylene produced in the MTO reactor is dimerized to make additional n-butenes. Furthermore, the ethylene, butenes, pentenes and hexenes are processed in a series of metathesis and isomerization reactors. The multitude of reactors and separations add to the complexity in the process and escalate the project cost. Another US patent also issued to UOP (U.S. Pat. No. 7,732,650) explains a similar process where the $C_4$ butenes are separated from the MTO reaction products, subjected to i-butene separation, isomerization and metathesis reactions with a portion of the ethylene produced in the MTO reactor. The heavier olefins produced in the MTO reactor is converted to light olefins in separate olefin cracking (OCP) reactor.

The present invention has found a new zeolite that has an improved selectivity toward propylene in the conversion of oxygenates to olefins. The new zeolite has improved deactivation, i.e. slower, properties which allows for longer residence times in the reactor and slower cycling of the catalyst through a regenerator. The new zeolite can also be used in fixed bed reactors, with reduced requirements for in-bed reactor regeneration.

The present invention is a process for the conversion of oxygenates to olefins. The process includes passing an oxygenate feedstream to an oxygenate conversion reaction operated at oxygenate conversion reaction conditions to generate a process stream comprising olefins. The oxygenate conversion reactor includes a catalyst for conversion. The catalyst is a zeolite having a microporous crystalline structure comprising a framework of $AlO_2$ and $SiO_2$ tetrahedral units, and an empirical composition in the as synthesized and anhydrous basis expressed by the empirical formula of:

$$M_m^{n+}R_r^{p+}AlSi_yO_z$$

where M is at least one exchangeable cation and R is at least one of an organoammonium cation, a quaternary phosphonium cation, and methonium cation. The catalyst has been further modified with silica or fluorine.

In the formula, "m" is the mole ratio of M to Al and varies from 0 to 3, "r" is the mole ratio of R to Al and has a value of about 0.1 to about 30, "n" is the weight average valence of M and has a value of about 1 to about 2, "p" is the weighted average valence of R and has a value of about 1 to about 2, "y" is the mole ratio of Si to Al and varies from greater than 32 to about 400. The value of "z" is the mole ratio of O to Al and has a value determined by the equation:

$$z=(m \cdot n + r \cdot p + 3 + 4 \cdot y)/2.$$

The zeolite can be further characterized by its x-ray diffraction pattern having at least the d spacing and intensities set forth in Table A:

TABLE A

| 2Θ | d(Å) | I/Io |
|---|---|---|
| 7.92-7.99 | 11.04-11.31 | m |
| 8.79-8.88 | 9.94-11.09 | m |
| 20.28-20.56 | 4.31-4.35 | w |
| 23.10-23.18 | 3.83-3.84 | vs |
| 23.86-24.05 | 3.69-3.72 | m |
| 29.90-30.05 | 2.97-2.98 | w |
| 45.02-45.17 | 2.00-2.01 | w |

The zeolite is also characterized by a high surface area and has a mesopore surface area between 140 m²/g and 400 m²/g.

M is selected from alkali and alkaline earth metals, where M is preferably one or more metals selected from lithium, sodium, potassium, cesium, strontium, calcium and barium. M can include a mixture of alkali and alkaline earth metals. R is one or more organoammonium cations that are quaternary ammonium cations, diquaternary ammonium cations, phosphonium cations, and methonium cations. Preferred R organoammonium cations include tetrabutylammonium, tetrabutylphosphonium, and hexamethonium.

In an alternate embodiment, the zeolite further comprises a microporous crystalline structure comprising a framework of $AlO_2$ and $SiO_2$ tetrahedral units, further including the element E and having the empirical composition in the as synthesized and anhydrous basis expressed by the empirical formula of:

$$M_m^{n+}R_r^{p+}Al_{1-x}E_xSi_yO_z.$$

In the formula "m" is the mole ratio of M to (Al+E) and varies from 0 to 3, "r" is the mole ratio of R to (Al+E) and has a value of about 0.1 to about 30, E is an element selected from the group consisting of gallium, iron, boron, indium and mixtures thereof, "x" is the mole fraction of E and has a value from 0 to 1.0, "y" is the mole ratio of Si to (Al+E) and varies from greater than 32 to about 200 and "z" is the mole ratio of O to (Al+E) and has a value determined by the equation:

$$z=(m \cdot n + r \cdot p + 3 + 4 \cdot y)/2.$$

The oxygenates in the oxygenate feedstream can include one or more of alcohols, aldehydes, ketones, ethers and carboxylic acids. A preferred oxygenate feedstream comprises methanol, dimethyl ether, or a mixture of methanol and dimethyl ether.

The oxygenate conversion reaction conditions include a temperature in the range from 300° C. to 600° C., and preferably between 300° C. to 550° C. The reaction conditions also includes an oxygenate partial pressure in the range from 100 kPa to 800 kPa. The pressure in the reactor can also be in terms of the partial pressure of the oxygenate. For methanol, the partial pressure is between 0 and 1.4 MPa, with a preferred partial pressure between 100 kPa and 800 kPa.

The process further includes passing the process stream from the oxygenate conversion reactor to an olefins recovery unit to generate an ethylene stream, a propylene stream, a $C_4$ stream, a $C_5$ stream, and a $C_{5+}$ heavies stream. Further processing downstream can include combining one or more of the $C_4$, $C_5$ and $C_{5+}$ streams, or operating the olefins recovery unit so as to not separate the $C_{4+}$ hydrocarbons.

An aspect of the invention includes upgrading the process stream through downstream process reactors to increase light olefin generation. One downstream process includes passing a portion of the ethylene stream with the $C_4$ stream, the $C_5$ stream, or a combination of the $C_4$ and $C_5$ streams to a metathesis unit to generate a metathesis effluent stream comprising propylene and/or butylenes. Another downstream process includes passing one or more the $C_4$ olefins stream, the $C_5$ olefins stream, the $C_{5+}$ olefins stream to an olefin cracking unit to generate an olefins cracking effluent stream comprising ethylene and propylene.

The present invention can be operated as a fixed bed reactor system for the oxygenate conversion reactor, or as a fluidized bed reactor system for the oxygenate conversion reactor.

The oxygenate conversion reactor can comprise a fluidized bed reactor wherein the oxygenate conversion reactor generates an effluent stream that includes the process fluid and the catalyst. The effluent stream is separated into a spent catalyst stream and a process stream comprising olefins. The spent catalyst stream is passed to a regenerator to generate a regenerated catalyst stream. The regenerated catalyst stream is passed to a stripper to generate a stripped catalyst stream wherein adsorbed residual carbon oxides have been removed. The stripped catalyst stream is then passed to the oxygenate conversion reactor.

The process using the new catalyst has displayed high propylene selectivity, in the range of 47% to 52%, and an uncharacteristically low ethylene selectivity of between 3% and 6% when tested under methanol to olefins (MTO) reaction conditions. Typical MFI catalysts reach similar but lower propylene selectivities or around 40%, while having higher ethylene selectivities, in the range from 10% to 20%. The unique and novel features of this material, which allows high propylene and low ethylene selectivity's, appears to result from the unique catalyst morphology (2-dimensional crystal size rather than the typical 3-D growth). This 2D crystal lattice appears to allow altered diffusion properties, which may affect the reaction mechanism leading to highly selective propylene formation without the production of high levels of ethylene.

In addition, it was discovered that external surface modifications with silica or fluorine can be utilized to boost the primary product yields via limiting externally catalyzed secondary reaction when reaction pressures are elevated. The surface modified materials may be modified using known methods, e.g. phosphorous doping, etc., within the art to allow improved or selectivated performance of the solid acid catalyst.

EXAMPLE 1

Layered Pentasil 1

An aluminosilicate reaction solution was prepared by first mixing 39.36 g of aluminum tri-sec-butoxide (95+%), 991.99 g tetrabutylammonium hydroxide (55 mass-% solution), and 800 g of ice water mixture while stirring vigorously. After thorough mixing, 1489.97 g tetraethyl orthosilicate was added. The reaction mixture was homogenized for an additional hour with a high speed mechanical stirrer. A composite aqueous solution containing 9.11 g of NaOH dissolved in 269.58 g distilled water was added, drop-wise, to the aluminosilicate solution. After the addition was completed, the resulting reaction mixture was homogenized for 1 hour, transferred to a 2000 ml Parr stainless steel autoclave which was heated to 115° C. and maintained at that temperature for 65 hrs. The solid product was recovered by centrifugation, washed with de-ionized water, and dried at 80° C.

The product was identified as a pentasil zeolite by powder x-ray diffraction. Representative diffraction lines observed for the product are shown in Table 1. The product composition was determined by elemental analysis to consist of the following mole ratios: Si/Al=42.1, Na/Al=0.85. A portion of the material was calcined by ramping to 560° C. for 5 hours followed by an 8 hour dwell in air. The BET surface area was 492 m$^2$/g, the micropore area was 273 m$^2$/g, the mesopore area was 219 m$^2$/g, the micropore volume was 0.14 cc/g, and mesopore volume was 0.99 cc/g. Scanning Electron Microscopy (SEM) revealed clusters of nano spheres of less than 20 nm. Chemical analysis was as follows: 1.02% Al, 44.6% Si, and 0.74% Na, Na/Al=0.85, Si/Al$_2$=84.2.

TABLE 1

| 2θ | d(Å) | I/I$_0$ % |
|---|---|---|
| 7.94 | 11.12 | m |
| 8.79 | 10.04 | m |
| 20.38 | 4.35 | w |
| 23.16 | 3.83 | vs |
| 23.86 | 3.72 | m |
| 29.96 | 2.98 | w |
| 45.07 | 2.00 | w |

EXAMPLE 2

Pentasil Layered Extrudates

The pentasil zeolite of example 1 was formulated into a catalyst containing 70% zeolite and 30% silica. In the catalyst preparation, the zeolite was mixed with LUDOX AS-40 and Hi-Sil 250 into a muller mixer. Additional water was added to the Muller mixer, while mixing, until dough with a proper texture for extrusion was formed. The dough was extruded to form 1/16" diameter cylinders, which were dried at 100° C. overnight and then sized to a length to diameter ratio of approximately 3. The dry extrudates was calcined in a box oven with a flowing air at 560° C. for 6 hours to remove the template. The calcined support was then exchanged using a 10 wt-% NH$_4$NO$_3$ solution at 75° C. for one hour. This was followed by water wash using 20 cc of water per cc of extrudates. The NH$_4$NO$_3$ exchange and water wash was repeated three more times. The extrudates was then dried at 120° C. for 4 hours and then activated at 550° C.

EXAMPLE 3

Fluorine Modified Layered 50 g of NH$_4$-extrudates from Example 2 was impregnated with a solution of NH$_4$HF$_2$ by dissolving 3 g of NH$_4$HF$_2$ in 100 g of water. The impregnation was done via evaporative impregnation. The F-extrudates were calcined at 507° C. for 2 hours with 3% steam. Fluoride analysis in the final catalyst was 2.29%.

EXAMPLE 4

Silica Modified Layered 50 g of NH$_4$-extrudates from Example 2 were treated with a solution of tetra orthosilicate and hexane. The hexane was removed and the sample was dry at 150° C. The Si-extrudates were calcined at 550° C.×2 hours. The silica deposition in the extrudates was 1.5%.

EXAMPLE 5

Standard Pentasil

An aluminosilicate reaction gel was prepared by first weighting 848.26 g of Ludox AS-40 colloidal silica in a 2-L beaker, and then added 138.10 g of tetrapropylammonium bromide solution (50%) was added. A composite aqueous solution containing 33.92 g of NaOH and 25.63 g of liquid sodium aluminate dissolved in 353.37 g distilled water was added drop-wise to the silicate solution. The final gel was allowed to mix for 20 minutes. The gel was transferred to a 2-L stirred reactor and heated to 125° C. for 72 hrs at 500 RPM. The solid was separated by centrifuge and washed 3 times with water, dried and determined by XRD to be a zeolite with a MFI structure.

The product composition was determined by elemental analysis to consist of the following mole ratios: Si/Al=41.4, Na/Al=0.66. A portion of the material was calcined by ramping to 560° C. for 5 hours followed by an 8 hour dwell in air. The BET surface area was 365 m$^2$/g, the micropore area was 310 m$^2$/g, the mesopore area was 55 m$^2$/g, the micropore volume was 0.161 cc/g, and mesopore volume was 0.52 cc/g. Scanning Electron Microscopy (SEM) revealed discrete and small crystal size between 20 to 50 nm. Chemical analysis was as follows: 1.06% Al, 45.6% Si, and 0.66% Na, Na/Al=0.66, Si/Al$_2$=82.4.

The standard pentasil zeolite of example 4 was calcined at 560° C. for 8 hours under nitrogen and then under air. The standard pentasil zeolite was then ammonium ion exchanged to exchange Na for NH$_{4+}$ by contacting 500 ml of 1 M NH$_4$NO$_3$ solution with 20 g of calcined standard pentasil zeolite at 80° C. and stirring for 1 hour. The product was then filtered and washed. The procedure was repeated three times. The final sodium level was 0.004%. This standard pentasil zeolite was then calcined at 550° C. in air for 2 h to convert $NH_4^+$ to $H^+$ by loss of ammonia.

EXAMPLE 6

Pentasil Extrudates

The pentasil zeolite of example 5 was formulated into a catalyst containing 70% zeolite and 30% silica. In the catalyst preparation, the zeolite was mixed with LUDOX AS-40 and Hi-Sil 250 into a muller mixer. Additional water was added to the muller, while mixing, until dough with a proper texture for extrusion was formed. The dough was extruded to form 1/16" diameter cylinders, which were dried at 100° C. overnight and then sized to a length to diameter ratio of approximately 3. The dry extrudates was calcined in a box oven with a flowing air at 560° C. for 6 hours to remove the template. The calcined support was then exchanged using a 10 wt-% $NH_4NO_3$ solution at 75° C. for one hour. This was followed by water wash using 20 cc of water per cc of extrudates. The $NH_4NO_3$ exchange and water wash was repeated three more times. The extrudates was then dried at 120° C. for 4 hours and then activated at 550° C.

EXAMPLE 7

Fluorine Modified 50 g of $NH_4$-extrudates from Example 6 was impregnated with a solution of $NH_4HF_2$ by dissolving 3 g of $NH_4HF_2$ in 100 g of water. The impregnation was done via evaporative impregnation. The F-extrudates were calcined at 507° C. for 2 hours with 3% steam. Fluoride analysis in the final catalyst was 0.83%.

EXAMPLE 8

Silica Modified 50 g of NH4-extrudates from Example 6 were treated with a solution of tetra orthosilicate and hexane. The hexane was removed and the sample was dry at 150° C. The Si-extrudates were calcined at 550° C.×2 hours. The silica deposition in the extrudates was 0.7%.

EXAMPLE 9

Fixed Bed Performance

Fixed bed pilot-plant test conditions and results are as follows. An 80/20 wt % solution of methanol/water was fed with an ISCO pump to a pre-heater for vaporization with suitable feed rate and catalyst loading (600 mg) to allow a WHSV (weight hourly space velocity) of 2.5 $h^{-1}$. The vaporized feed was then carried via inert carrier gas ($N_2$) through a fixed bed micro-reactor maintained at suitable pressure to allow a 40 psig methanol partial pressure. Reactor temperature was controlled at 435° C. The resulting performance values at 9 hours on stream were obtained for the materials prepared in Examples 2-4 and 6-8:

| Sample | Si/Al$_2$ | Conversion | $C_2^=$ % | $C_3^=$ % | $C_3^=/C_2^=$ |
|---|---|---|---|---|---|
| Layered Pentasil Extrudate (ex2) | 71 | 100 | 5.1 | 13.0 | 2.6 |
| Standard Pentasil Extrudate (ex6) | 80 | 100 | 3.3 | 7.1 | 2.1 |
| Silica Treated Layered Pentasil Extrudate (ex4) | 71 | 100 | 5.9 | 15.7 | 2.7 |
| Silica Treated Standard Pentasil Extrudate (ex8) | 80 | 100 | 4.0 | 8.6 | 2.1 |
| Fluorine Treated Layered Pentasil Extrudate (ex3) | 71 | 100 | 6.1 | 19.3 | 3.2 |
| Fluorine Treated Standard Pentasil Extrudate (ex7) | 80 | 100 | 5.1 | 11.2 | 2.2 |

Note that selectivity values listed are all obtained at identical time on stream with 100% conversion (methanol+DME). Selectivity values are given as wt % component. From this data it can be observed that addition of catalyst surface modification (silica or fluorine treated) allows increases in performance over the un-treated sample for both the standard pentasil and the layered pentasil. Furthermore, the layered pentasil and its surface treated analogues display improved light olefin selectivity (ethylene plus propylene), and $C_3^=/C_2^=$ ratio compared to the modified and un-modified standard pentasil benchmark materials.

While the invention has been described with what are presently considered the preferred embodiments, it is to be understood that the invention is not limited to the disclosed embodiments, but it is intended to cover various modifications and equivalent arrangements included within the scope of the appended claims.

What is claimed is:

1. A process for the conversion of oxygenates to olefins comprising:

passing an oxygenate feedstream to an oxygenate conversion reactor operated at oxygenate conversion reaction conditions, wherein the reactor includes a catalyst having a layered pentasil structure and wherein the surface of the catalyst has been modified with silica or fluorine, to generate a process stream comprising olefins, wherein the catalyst is a zeolite having a microporous crystalline structure comprising a framework of $AlO_2$ and $SiO_2$ tetrahedral units, and an empirical composition in the as synthesized and anhydrous basis expressed by the empirical formula of:

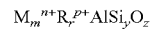

$$M_m^{n+}R_r^{p+}AlSi_yO_z$$

where M is at least one exchangeable cation selected from the group consisting of alkali and alkaline earth metals, "m" is the mole ratio of M to Al and varies from 0 to 3, R is at least one organoammonium cation selected from the group consisting of quaternary ammonium cations, diquaternary ammonium cations, quaternary phosphonium cations, methonium cations, and mixtures thereof, "r" is the mole ratio of R to Al and has a value of about 0.1 to about 30, "n" is the weight average valence of M and has a value of about 1 to about 2, "p" is the weighted average valence of R and has a value of about 1 to about 2, "y" is the mole ratio of Si to Al and varies from greater than 32 to about 200 and "z" is the mole ratio of O to Al and has a value determined by the equation:

$$z=(m \cdot n+r \cdot p+3+4 \cdot y)/2 \text{:and}$$

wherein the zeolite is further characterized in that it has the x-ray diffraction pattern having at least the d spacing and intensities set forth in the following Table A:

TABLE A

| 2Θ | d(Å) | I/Io |
|---|---|---|
| 7.92-7.99 | 11.04-11.31 | m |
| 8.79-8.88 | 9.94-11.09 | m |
| 20.28-20.56 | 4.31-4.35 | w |
| 23.10-23.18 | 3.83-3.84 | vs |
| 23.86-24.05 | 3.69-3.72 | m |
| 29.90-30.05 | 2.97-2.98 | w |
| 45.02-45.17 | 2.00-2.01 | w. |

2. The process of claim 1 wherein the zeolite has a mesopore surface area between 140 m²/g and 400 m²/g.

3. The process of claim 1 wherein the zeolite further comprises a microporous crystalline structure comprising a framework of $AlO_2$ and $SiO_2$ tetrahedral units, further including the element E and having the empirical composition in the as synthesized and anhydrous basis expressed by the empirical formula of:

$$M_m^{n+}R_r^{p+}Al_{1-x}E_xSi_yO_z$$

where "m" is the mole ratio of M to (Al+E) and varies from 0 to 3, "r" is the mole ratio of R to (Al+E) and has a value of about 0.1 to about 30, E is an element selected from the group consisting of gallium, iron, boron, indium and mixtures thereof, "x" is the mole fraction of E and has a value from 0 to 1.0, "y" is the mole ratio of Si to (Al+E) and varies from greater than 32 to about 200 and "z" is the mole ratio of O to (Al+E) and has a value determined by the equation:

$$z=(m \cdot n+r \cdot p+3 +4 \cdot y)/2.$$

4. The process of claim 1 further comprising separating the process stream into an ethylene stream, a propylene stream, a $C_4$ stream, a $C_5$ stream, and a $C_{5+}$ heavies stream, or some combination thereof.

5. The process of claim 4 further comprising passing the heavies stream, comprising $C_{4+}$ olefins, to an olefin cracking unit, or passing the $C_4$ stream and/or the $C_4^+$ stream to a metathesis unit along with some portion or all of the ethylene stream.

6. The process of claim 1 wherein the oxygenates comprise alcohols, aldehydes, ethers and mixtures thereof.

7. The process of claim 6 wherein the oxygenate comprises methanol.

8. The process of claim 1 wherein oxygenate conversion reactor comprises a fluidized reactor bed, and wherein the oxygenate conversion reactor generate an effluent stream comprising catalyst and a process fluid, wherein the effluent stream is separated into a spent catalyst stream and the process stream comprising olefins.

9. The process of claim 8 wherein the catalyst stream is passed to a regenerator to generate a regenerated catalyst stream.

10. The process of claim 9 further comprising passing the regenerated catalyst stream to a stripper, to generate a stripped catalyst stream comprising catalyst with carbon oxides removed.

11. The process of claim 10 further comprising passing the stripped catalyst stream to the oxygenate conversion reactor.

12. The process of claim 1 wherein the oxygenate conversion reaction conditions include a temperature in the range from 300° C. to 600° C.

13. The process of claim 1 wherein the oxygenate conversion reaction conditions include an oxygenate partial pressure in the range from 100 kPa to 800 kPa.

14. A process for the conversion of oxygenates to olefins comprising:
passing an oxygenate feedstream to an oxygenate conversion reactor operated at oxygenate conversion reaction conditions, wherein the reactor includes a catalyst having a 2-D layered pentasil structure and wherein the surface of the catalyst has been modified with silica or fluorine, to generate a process stream comprising olefins, wherein the catalyst is a zeolite having a microporous crystalline structure comprising a framework of $AlO_2$ and $SiO_2$ tetrahedral units, and having the empirical composition in the as synthesized and anhydrous basis expressed by the empirical formula of:

$$M_m^{n+}R_r^{p+}Al_{1-x}E_xSi_yO_z;$$

wherein M is at least one exchangeable cation selected from the group consisting of alkali and alkaline earth metals, m" is the mole ratio of M to (Al+E) and varies from 0 to 1, R is at least one organoammonium cation selected from the group consisting of quaternary ammonium cations, diquaternary ammonium cations, quaternary phosphonium cations, methonium cations, and mixtures thereof, "r" is the mole ratio of R to (Al+E) and has a value of 0.1 to about 30, "n" is the weight average valence of M and has a value of 1 to 2, "p" is the weighted average valence of R and has a value of 1 to 2, E is an element selected from the group consisting of gallium, iron, boron, indium and mixtures thereof, "x" is the mole fraction of E and has a value from 0 to 1.0, "y" is the mole ratio of Si to (Al+E) and varies from greater than 32 to about 200 and "z" is the mole ratio of O to (Al+E) and has a value determined by the equation:

$$z=(m \cdot n+r \cdot p+3 +4 \cdot y)/2$$

and it is characterized in that it has the x-ray diffraction pattern having at least the d spacing and intensities set forth in the following Table A:

TABLE A

| 2Θ | d(Å) | I/Io |
|---|---|---|
| 7.92-7.99 | 11.04-11.31 | m |
| 8.79-8.88 | 9.94-11.09 | m |
| 20.28-20.56 | 4.31-4.35 | w |
| 23.10-23.18 | 3.83-3.84 | vs |
| 23.86-24.05 | 3.69-3.72 | m |
| 29.90-30.05 | 2.97-2.98 | w |
| 45.02-45.17 | 2.00-2.01 | w. |

15. The process of claim 14 wherein the oxygenate conversion reaction conditions include a temperature in the range from 300° C. to 600° C.

16. The process of claim 14 wherein the oxygenate conversion reaction conditions include an oxygenate partial pressure in the range from 100 kPa to 800 kPa.

17. The process of claim 14 further comprising separating the process stream into an ethylene stream, a propylene stream, a $C_4$ stream, a $C_5$ stream, and a $C_{5+}$ heavies stream, or some combination thereof.

18. The process of claim 17 further comprising passing the heavies stream, comprising C4+ olefins, to an olefin cracking unit, or passing the $C_4$ stream and/or the $C_4^+$ stream to a metathesis unit along with some portion or all of the ethylene stream.

19. The process of claim 14 wherein the oxygenates comprises methanol.

* * * * *